US00PP17708P3

(12) United States Plant Patent
Kawashima

(10) Patent No.: US PP17,708 P3
(45) Date of Patent: May 8, 2007

(54) **NEW GUINEA *IMPATIENS* PLANT NAMED 'MISATO FG1'**

(50) Latin Name: *Impatiens×hybrida*
Varietal Denomination: Misato FG1

(75) Inventor: Moriya Kawashima, Nagano-ken (JP)

(73) Assignee: Sakata Seed Corporation, Yokohama (JP)

( * ) Notice: Subject to any disclaimer, the term of this patent is extended or adjusted under 35 U.S.C. 154(b) by 27 days.

(21) Appl. No.: 11/242,356

(22) Filed: Oct. 3, 2005

(65) Prior Publication Data

US 2007/0079413 P1 Apr. 5, 2007

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—Annette H Para
(74) *Attorney, Agent, or Firm*—Jondle & Associates, P.C.

(57) ABSTRACT

A New Guinea *Impatiens* cultivar particularly distinguished by its high blooming temperature and large red flowers is disclosed.

1 Drawing Sheet

Genus and species: *Impatiens×hybrida.*
Variety denomination: 'Misato FG1'.

BACKGROUND OF THE NEW PLANT

The present invention comprises a new and distinct cultivar of New Guinea *Impatiens,* botanically known as *Impatiens×hybrida,* and hereinafter referred to by the cultivar name 'Misato FG1'. 'Misato FG1' originated from an interspecific hybridization between *Impatiens* '02-NG2', an unpatented proprietary orange-flowered *impatiens* breeding line and *Impatiens* '02-NG1', an unpatented proprietary pink-lilac-flowered *impatiens* breeding line in Misato, Japan. In 2002, the two *Impatiens* species were crossed and a population of $F_1$ plants was created.

The $F_1$ plants were evaluated in Misato, Japan in 2004 in an open field trial. Criteria for selection included mounding growth habit, tolerance to heat and cold, vigorous rooting, red flower color and overall plant vigor. At the end of the trial, one single-plant selection was made based on the above criteria and vegetatively propagated. The plant was trialed in Athens, Ga. and Salinas, Calif. The selection subsequently was named 'Misato FG1' and found to retain its distinctive characteristics through successive asexual propagations.

Plant Breeder's Rights for this cultivar were applied for in Canada on Apr. 19, 2005. No sales or offers for sale of this cultivar were made before Apr. 19, 2005.

SUMMARY OF THE INVENTION

The following are the most outstanding and distinguishing characteristics of this new cultivar when grown under normal horticultural practices in Salinas, Calif.

1. Red flower color
2. Tolerance to heat and cold
3. Vigorous rooting
4. Overall plant vigor

DESCRIPTION OF PHOTOGRAPHS

This new *impatiens* plant is illustrated by the accompanying photographs which show overall plant habit including blooms, buds, and foliage of the plant; the colors shown are as true as can be reasonably obtained by conventional photographic procedures.

Figure 1:
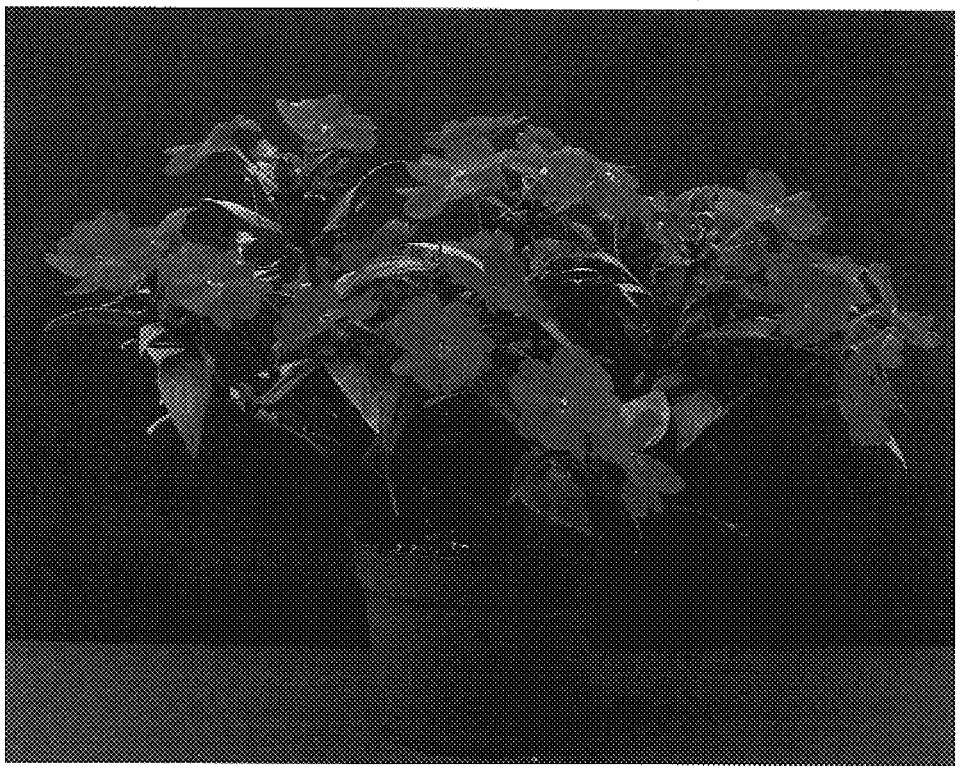

FIG. 1. The photograph shows overall plant habit including blooms, buds and foliage.

Figure 2:
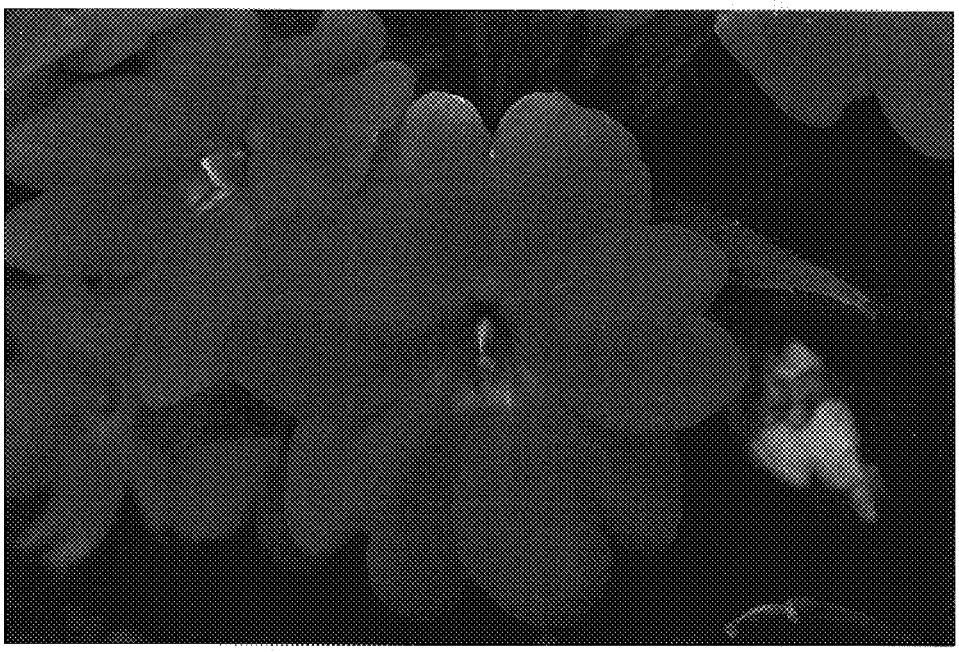

FIG. 2. The photograph shows the mature inflorescence.

DETAILED DESCRIPTION OF THE NEW CULTIVAR

The following detailed descriptions set forth the distinctive characteristics of 'Misato FG1'. The data which define these characteristics were collected from asexual reproductions carried out in Salinas, Calif. The plant history was taken on plants grown for about four months from propagation by terminal cuttings under greenhouse conditions. Color references are primarily to The R.H.S. Colour Chart of The Royal Horticultural Society of London (R.H.S.), $4^{th}$ edition (2001). Anatomic labels are from *The Cambridge Illustrated Glossary of Botanical Terms* by M. Hickey and C. Kink, Cambridge University Press.

DETAILED BOTANICAL DESCRIPTION

Classification:
- *Family.*—Balsaminaceae.
- *Botanical.*—*Impatiens* interspecific cross (*Impatiens×hybrida*).
- *Common name.*—*Impatiens.*

Parentage:
- *Female parent.*—'02-NG2', a proprietary *Impatiens* breeding line (unpatented).
- *Male parent.*—'02-NG1', a proprietary *Impatiens* breeding line (unpatented).

Growth:

*Time to produce a rooted cutting.*—The terminal 0.1 to 1.5 inches of an actively growing stem was excised. The base of the cuttings were dipped for 1 to 2 seconds in a 1:9 solution of DIP 'N GROW (1 solution: 9 water) root-inducing solution immediately prior to sticking into the cell trays. Cuttings were stuck into plastic cell trays having 98 cells and containing a moistened peat moss-based growing medium. The cuttings were misted with water from overhead for 10 seconds every 30 minutes until sufficient roots were formed. The vegetative cuttings were propagated in five to six weeks.

*Environmental conditions for plant growth.*—Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

*Time to bloom from propagation.*—6–8 weeks.

Plant description:

*Habit.*—Upright and branching.

*Height.*—23.0–26.0 cm as measured from soil line to top of foliage.

*Spread.*—35.0–38.0 cm.

*Time to produce a finished flowering plant.*—6–8 weeks.

*Outdoor plant performance.*—Will flower as long as the temperature is above 5° C.

*Temperature tolerance.*—Plants have been observed to continuously flower at a temperature range of 5° C.–36° C.

*Life cycle.*—Tender perennial.

*Time to initiate and develop roots.*—About 4 weeks.

Branches:

*Number.*—5–6 per plant.

*Length.*—15.0 cm.

*Diameter.*—0.5–0.7 cm.

Stems:

*Length.*—6.0–7.0 cm.

*Diameter.*—0.7–0.9 cm.

*Internode length.*—4.5–6.0 cm.

*Color.*—Nearest to RHS 59A (red-purple).

*Stem description.*—Strong; circular cross-section.

*Pubescence.*—Absent.

*Stem anthocyanin.*—Absent.

*Pedicels texture.*—Dull, slightly pubescent.

*Peduncles.*—Length: 5.0–5.4 cm. Color: RHS 58A (red-purple) with RHS 165C (grayed-orange) base. Texture: Dull, slightly pubescent.

Leaves:

*Arrangement.*—Opposite if two leaves are at one node and whorled if more than two leaves are at one node.

*Length.*—8.7–9.2 cm.

*Width.*—3.1–3.5 cm.

*Shape.*—Lanceolate.

*Margin.*—Serrate.

*Apex.*—Acuminate.

*Base.*—Attenuate.

*Color.*—Upper surface: RHS 136A (green). Lower surface: RHS 191A (grayed-green) with RHS 60A (red-purple) splotches.

*Texture.*—Dull and sticky.

*Variegation.*—Absent.

*Fragrance.*—Absent.

*Pubescence.*—Slight.

*Pubescence color.*—RHS N155A (white).

*Venation color.*—Upper surface: RHS 60A (red-purple). Lower surface: RHS 60A (red-purple).

*Petioles.*—Length: 0.8–1.0 cm. Color: RHS 60A (red-purple). Texture: Dull, slightly pubescent.

Flower buds:

*Shape.*—Deltoid (longitudinal cross-section).

*Length.*—1.1–1.2 cm.

*Diameter.*—0.8–1.1 cm.

*Color.*—RHS N77A (purple) fading to RHS 53C (red).

*Texture.*—Glabrous.

Inflorescence:

*Blooming habit.*—Will flower as long as the temperature is above 5° C.

*Inflorescence type.*—Single flower with spur.

*Number of flowers per node.*—3–5 in bloom at any one time with about 10 buds.

*Number of flowers per plant.*—10–25, depends on amount of pinching during growth.

*Flower form.*—Roughly circular with 5 radial petals.

*Lastingness of individual blooms on the plant.*—Greater than 14 days (no upper limit observed yet).

*Fragrance.*—Absent.

Flowers:

*Immature flower.*—Color: Same as mature flower (color does not darken or fade over time).

*Mature flower.*—Color: Upper surface: Closest to RHS 46C (red). Lower surface: Closest to RHS 58C (red). Eye zone: 60D (red-purple). Diameter: 6.5 cm. Depth: 0.1–0.3 cm.

Petals:

*Shape.*—Obcordate.

*Length.*—2.1–2.5 cm.

*Width.*—2.7–3.0 cm.

*Apex.*—Emarginate (cleaved).

*Base.*—Attenuate.

*Margin.*—Entire.

*Petal texture.*—Glabrous.

*Color.*—Upper surface: Closest to RHS 46C (red). Lower surface: RHS 58C (red-purple). Eye zone: RHS 60D (red-purple).

Spur:

*Shape.*—Tubular and curved downward.

*Color.*—RHS 58C (red-purple).

*Length.*—4.6–5.2 cm.

*Diameter.*—0.2–0.3 cm.

Sepals:

*Shape.*—Lanceolate.

*Apex.*—Caudate.

*Base.*—Subcordate.

*Margin.*—Entire.

*Texture.*—Dull.

Reproductive organs:

*Stamens.*—Form: Fused; split into 4 lobes. Number: Many. Filament color: RHS 71B (red-purple). Anther color: RHS N155A (white). Pollen amount: Heavy. Pollen color: RHS N155A (white). Pollen description: Powdery.

*Pistils.*—Number: 5. Stigma color: RHS 144A (yellow-green). Style color: RHS 144A (yellow-green).

*Ovary arrangement.*—Parietal.

*Fruit/seed set.*—Little to none observed.

Disease and insect resistance: None observed.

COMPARISON WITH KNOWN CULTIVARS

'Misato FG1' differs from the female parent, '02-NG2', a proprietary *Impatiens* breeding line (unpatented), in that 'Misato FG1' has red flowers while '02-NG2' has orange flowers.

'Misato FG1' differs from the male parent, '02-NG1', a proprietary *Impatiens* breeding line (unpatented), in that 'Misato FG1' has red flowers while '02-NG1' has pink-lilac flowers.

'Misato FG1' is similar to the commercial *Impatiens* cultivar 'Balfafusia' (U.S. Plant Pat. No. 12,588) (known commercially as 'Fanfare Fuschia') however there are differences as shown in the table below.

TABLE 1

Comparison of Characteristics between 'Misato FG1' and 'Balfafusia'

| Characteristic | 'Misato FG1' | 'Balfafusia' |
|---|---|---|
| Growth habit | Upright, branching | Trailing |
| Flowering temperature | Can flower above 30° C. | Cannot flower above 30° C. |
| Flower diameter | About 6.5 cm | About 5 cm |
| Petal color, Upper surface | Closest to RHS 46C | Closest to RHS 74A but bluer |

I claim:

1. A new and distinct cultivar of New Guinea *Impatiens* plant as shown and described herein.

* * * * *